United States Patent
Orbay et al.

(12) 
(10) Patent No.: US 9,622,799 B2
(45) Date of Patent: Apr. 18, 2017

(54) FORMABLE BONE PLATE, CLAMPING APPARATUS, OSTEOTOMY SYSTEM AND METHOD FOR RECONSTRUCTING A BONE

(75) Inventors: Jorge L. Orbay, Miami, FL (US); Thomas H. Norman, Miami, FL (US); William Garcia de Quevedo, Miami, FL (US)

(73) Assignee: Skeletal Dynamics, LLC., Miami, FL (US)

( * ) Notice: Subject to any disclaimer, the term of this patent is extended or adjusted under 35 U.S.C. 154(b) by 1276 days.

(21) Appl. No.: 12/463,037

(22) Filed: May 8, 2009

(65) Prior Publication Data

US 2009/0281543 A1    Nov. 12, 2009

Related U.S. Application Data

(60) Provisional application No. 61/051,749, filed on May 9, 2008.

(51) Int. Cl.
| | | |
|---|---|---|
| *A61B 17/80* | (2006.01) | |
| *A61B 17/88* | (2006.01) | |
| *A61B 17/17* | (2006.01) | |
| *A61B 90/00* | (2016.01) | |

(52) U.S. Cl.
CPC .......... *A61B 17/80* (2013.01); *A61B 17/808* (2013.01); *A61B 17/8085* (2013.01); *A61B 17/8863* (2013.01); *A61B 17/1728* (2013.01); *A61B 17/8897* (2013.01); *A61B 2090/034* (2016.02)

(58) Field of Classification Search
CPC ... A61B 17/80; A61B 17/808; A61B 17/8085; A61B 17/8863; A61B 17/1728; A61B 17/8897

USPC .... 606/70, 281–283, 284, 324, 99, 101, 104
See application file for complete search history.

(56) References Cited

U.S. PATENT DOCUMENTS

| | | | | |
|---|---|---|---|---|
| 4,263,903 A | * | 4/1981 | Griggs | 606/75 |
| 5,423,826 A | * | 6/1995 | Coates et al. | 606/96 |
| 5,607,427 A | * | 3/1997 | Tschakaloff | 606/284 |
| 5,667,513 A | * | 9/1997 | Torrie et al. | 606/104 |
| 6,036,692 A | * | 3/2000 | Burel et al. | 606/86 A |
| 6,077,271 A | | 6/2000 | Huebner et al. | |
| 6,436,103 B1 | * | 8/2002 | Suddaby | 606/96 |
| 6,648,888 B1 | * | 11/2003 | Shluzas | 606/86 A |

(Continued)

FOREIGN PATENT DOCUMENTS

| | | |
|---|---|---|
| EP | 1247494 A1 | 10/2002 |
| WO | 9511632 A1 | 5/1995 |

OTHER PUBLICATIONS

International Search Report and written opinion dated Jan. 11, 2010.

*Primary Examiner* — Zade Coley
(74) *Attorney, Agent, or Firm* — Laurence A. Greenberg; Werner H. Stemer; Ralph E. Locher

(57) ABSTRACT

A system and method are provided that use a formable bone plate and a clamping apparatus for small bone reconstruction. The formable bone plate includes a plate body having a plurality of nodes separated by internodes. Each node includes a hole formed therein for receiving a screw, wire, tack, or other fixation device screwed or placed into a bone. A clamp engages an engagement section of the node to facilitate bending of at least one of the internodes to contour the plate to the bone in-situ or ex-situ and when at least partly screwed to or not screwed to the bone.

14 Claims, 13 Drawing Sheets

(56) References Cited

U.S. PATENT DOCUMENTS

| | | |
|---|---|---|
| 6,755,832 B2 | 6/2004 | Happonen et al. |
| 6,923,814 B1 | 8/2005 | Hildebrand et al. |
| 7,166,111 B2 * | 1/2007 | Kolb et al. ............... 606/96 |
| 7,189,237 B2 | 3/2007 | Huebner |
| 7,229,446 B2 * | 6/2007 | Capanni .................. 606/86 R |
| 7,273,481 B2 * | 9/2007 | Lombardo et al. ......... 606/86 A |
| 7,357,804 B2 * | 4/2008 | Binder et al. ............. 606/96 |
| 7,473,255 B2 * | 1/2009 | McGarity et al. ......... 606/86 B |
| 2003/0055429 A1 * | 3/2003 | Ip et al. .................. 606/69 |
| 2004/0068269 A1 * | 4/2004 | Bonati et al. ............. 606/104 |
| 2004/0102777 A1 * | 5/2004 | Huebner .................. 606/69 |
| 2004/0176780 A1 * | 9/2004 | Knopfle et al. ........... 606/105 |
| 2006/0036254 A1 * | 2/2006 | Lim ....................... 606/86 |
| 2006/0122607 A1 * | 6/2006 | Kolb ...................... 606/71 |
| 2006/0161158 A1 | 7/2006 | Orbay et al. |
| 2007/0129731 A1 * | 6/2007 | Sicvol et al. ............. 606/104 |
| 2007/0213726 A1 * | 9/2007 | McGarity et al. ......... 606/69 |
| 2007/0233111 A1 | 10/2007 | Orbay et al. |
| 2007/0233112 A1 * | 10/2007 | Orbay et al. ............. 606/69 |

* cited by examiner

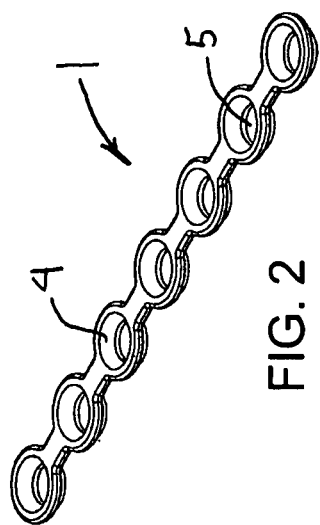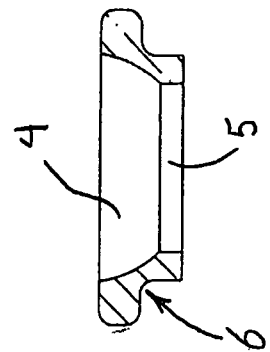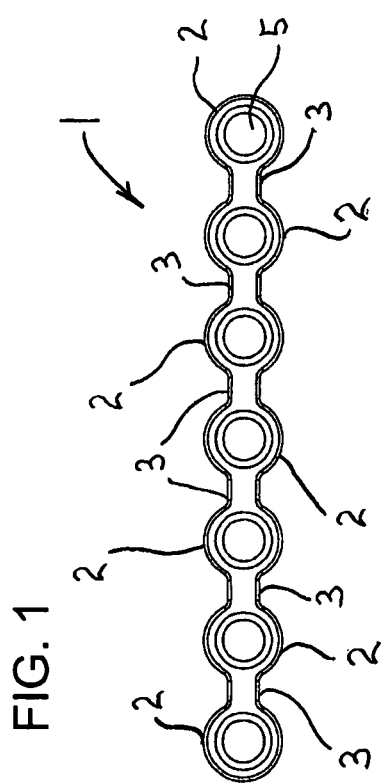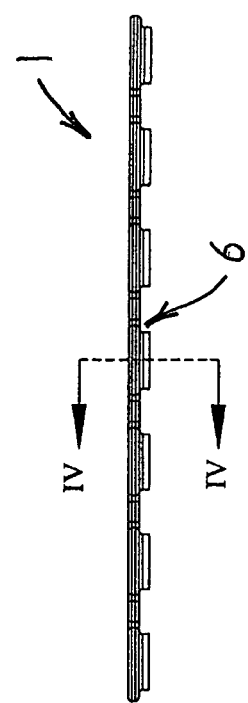

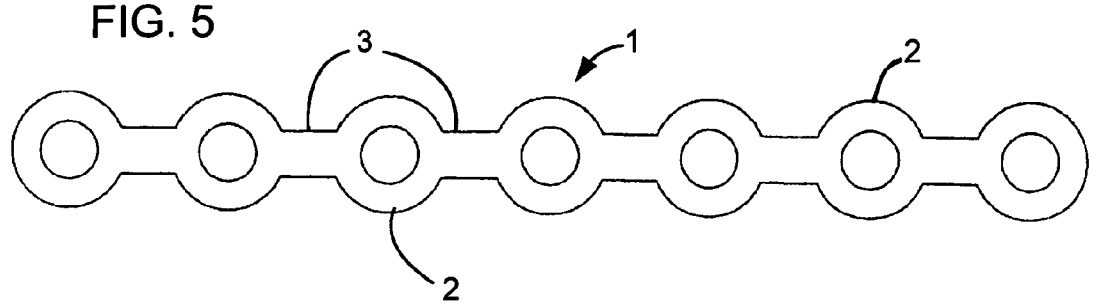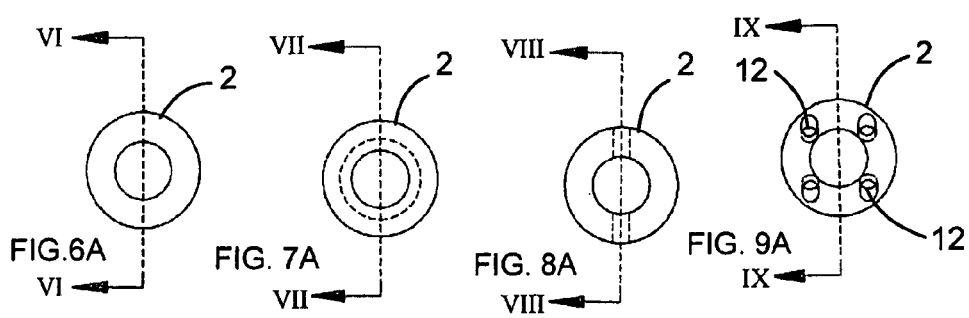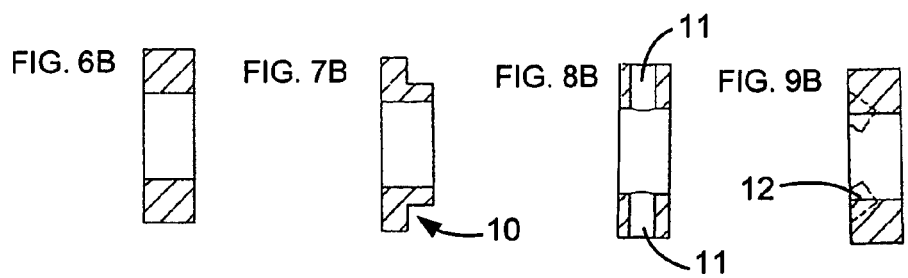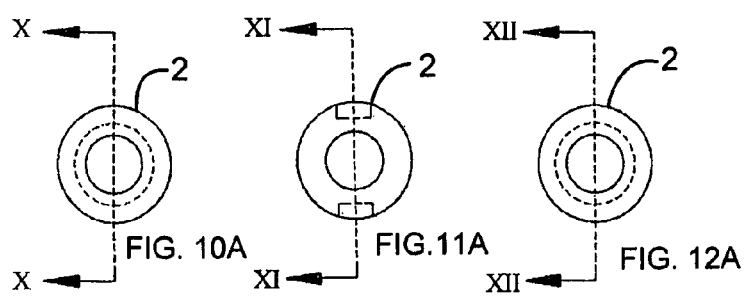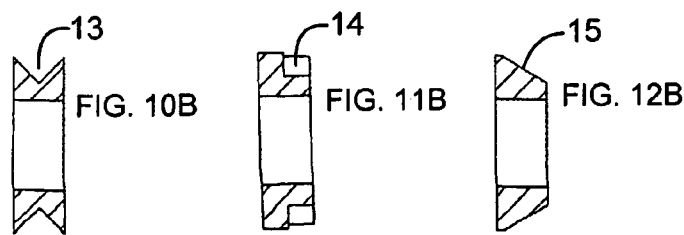

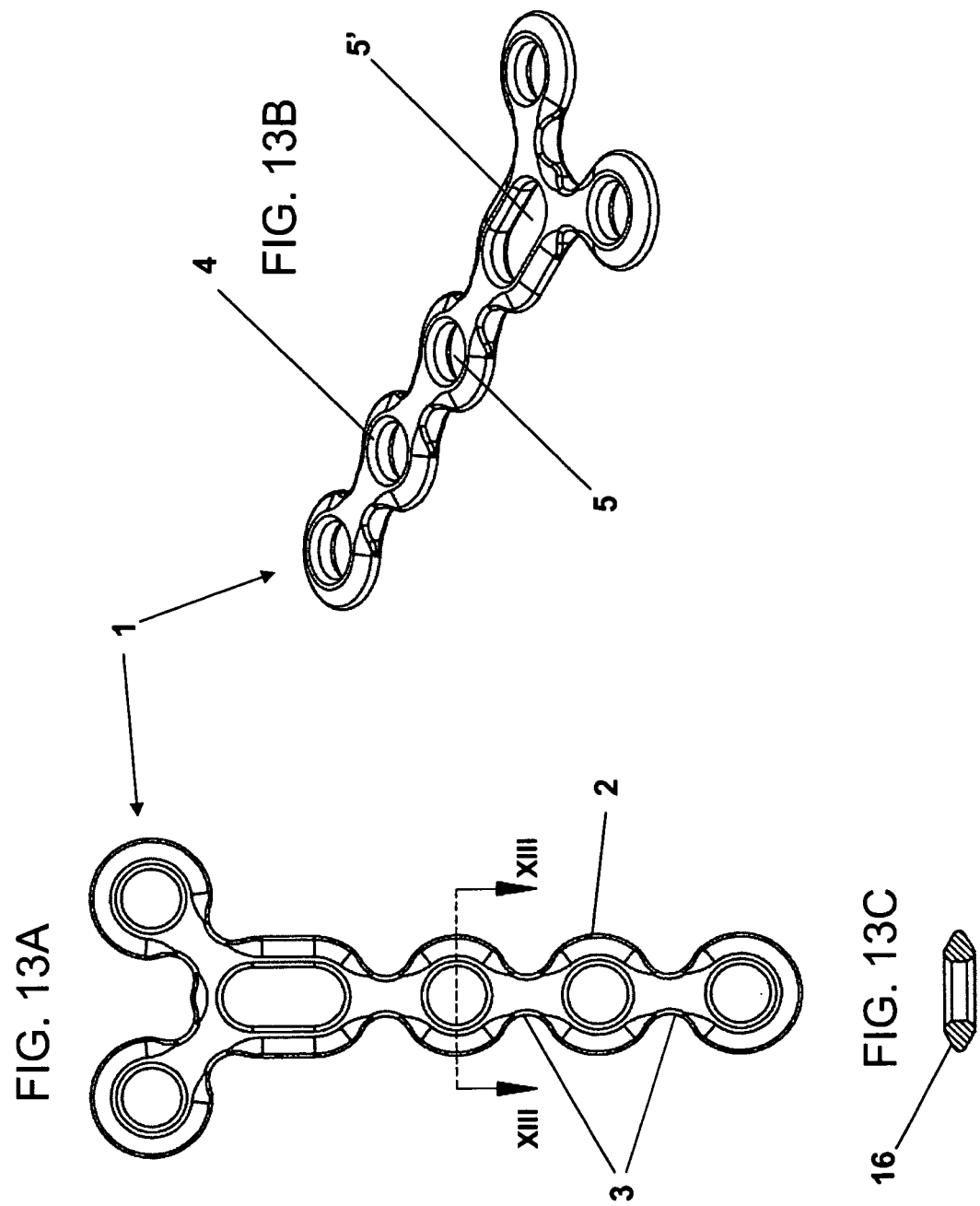

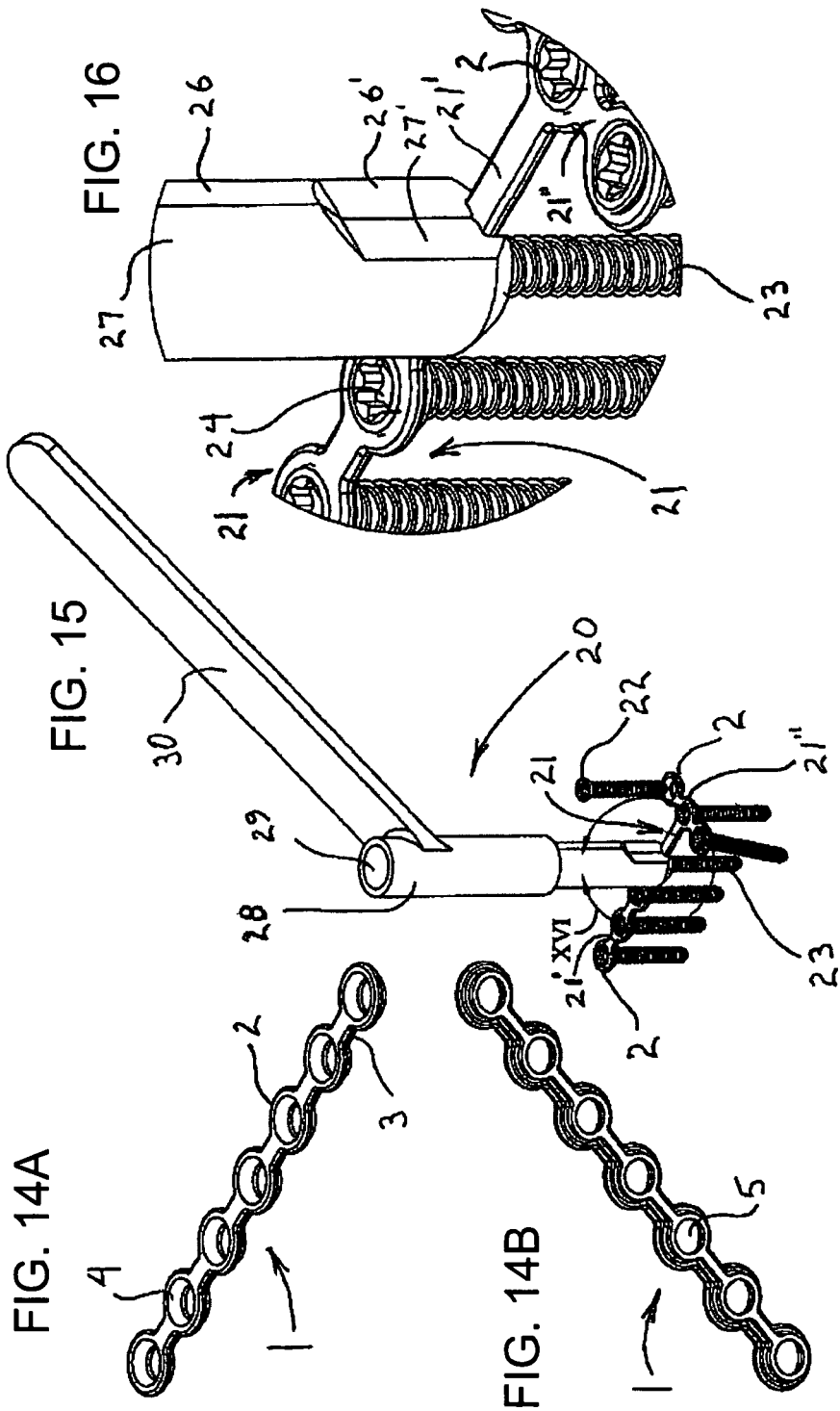

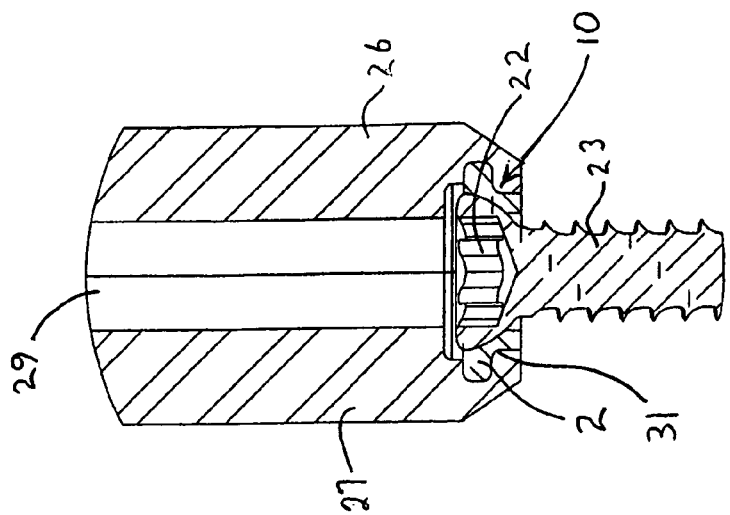
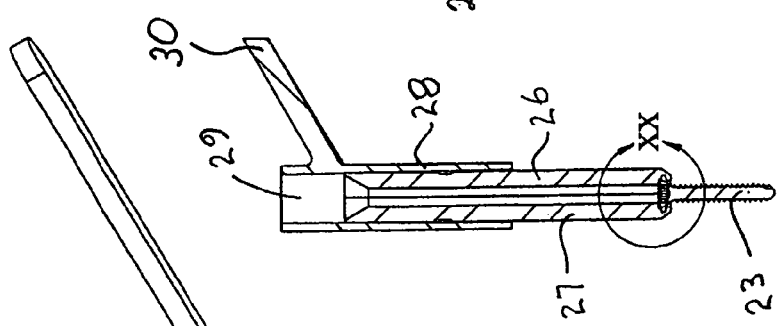
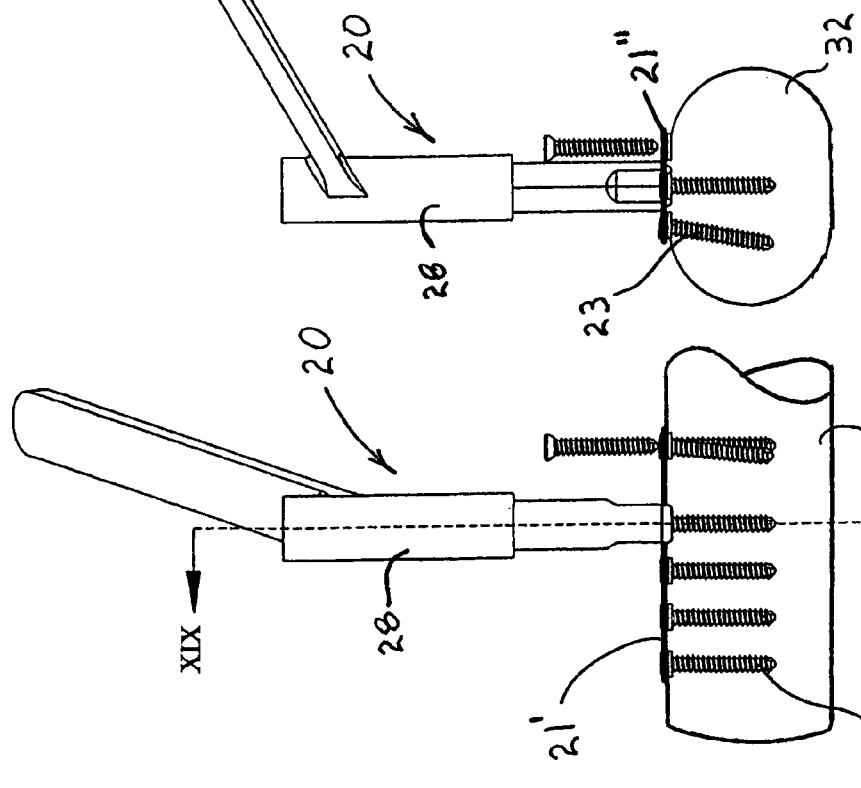
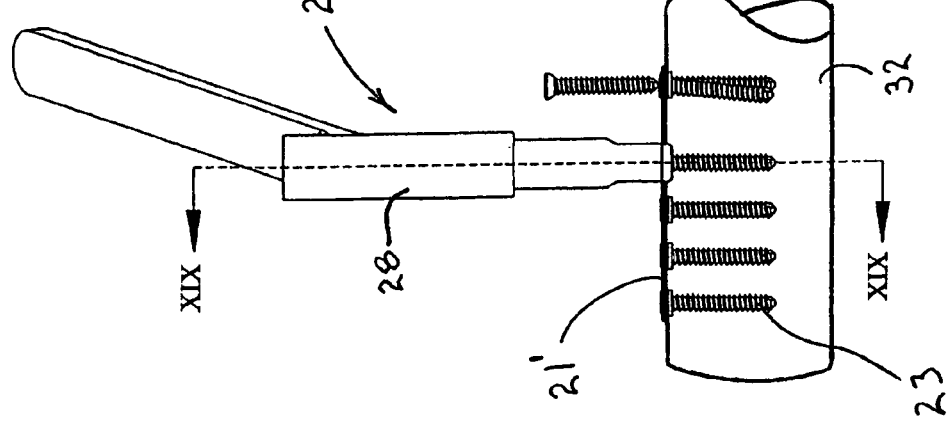
FIG. 17
FIG. 18
FIG. 19
FIG. 20

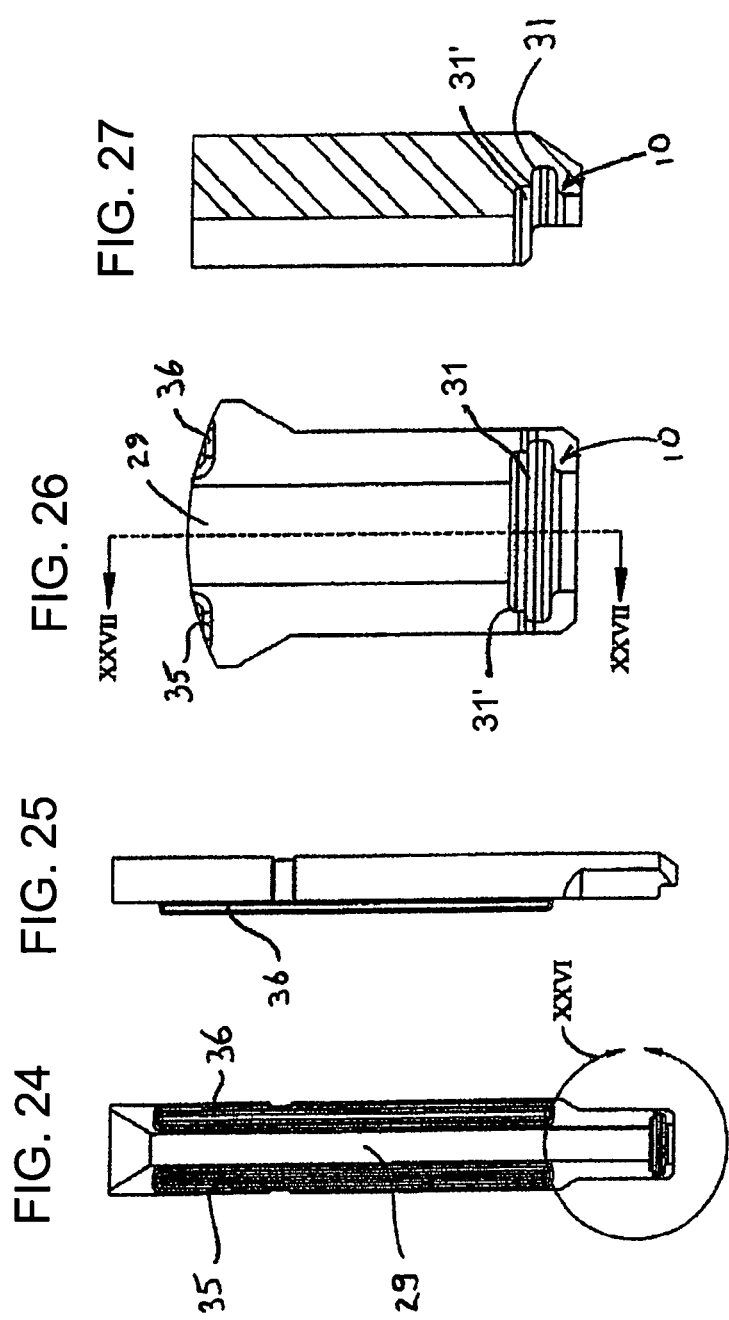

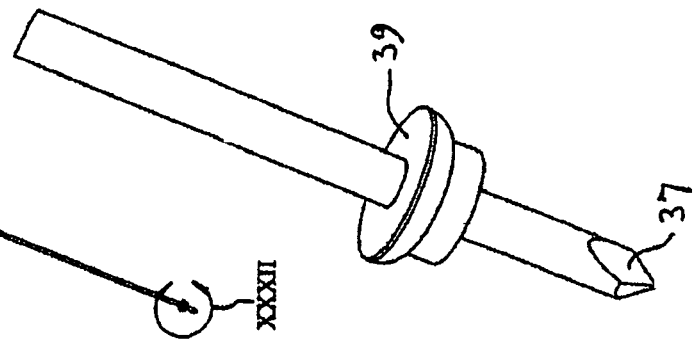
FIG. 31
FIG. 32
FIG. 30
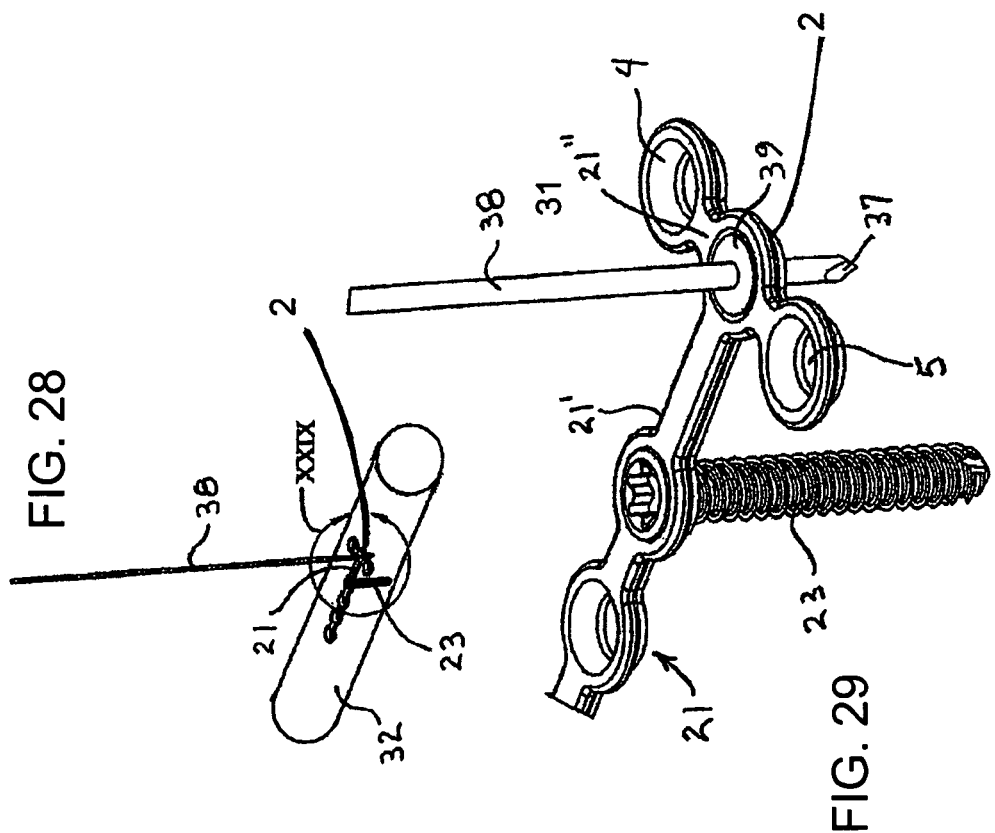
FIG. 28
FIG. 29

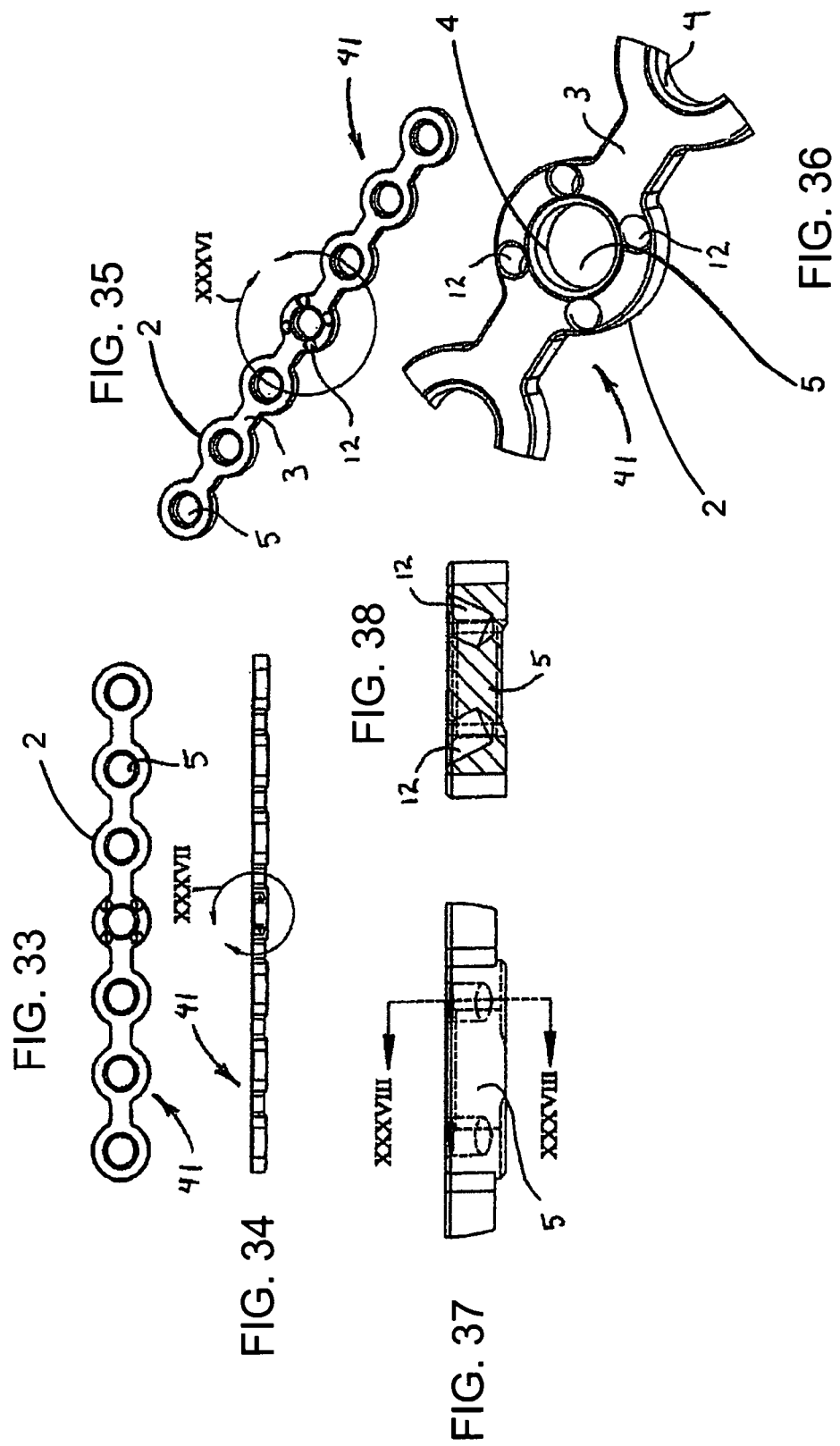

FORMABLE BONE PLATE, CLAMPING APPARATUS, OSTEOTOMY SYSTEM AND METHOD FOR RECONSTRUCTING A BONE

CROSS-REFERENCE TO RELATED APPLICATION

The present application claims priority to the Provisional Patent Application No. 61/051,749, filed on May 9, 2008 and entitled "Formable Bone Plate, Clamping Apparatus, Osteotomy System And Method For Reconstructing A Bone", which application is being incorporated herein, by reference, in its entirety.

BACKGROUND OF THE INVENTION

Field of the Invention

The invention relates to a formable bone plate, a clamping apparatus, an osteotomy system and a method for small bone reconstruction. Such a plate, apparatus, system and method provide a surgeon with implants and instruments necessary to perform reconstructive bone surgery (osteotomies and fusions) of the small bones of the upper extremity or other parts of the human body, which could eventually include wrist, hand, maxillofacial, foot and ankle surgery.

Description of the Related Art

Typical formable bone plates are formed of nodes that provide for screw or pin type of mechanical attachment to the bone and internodes or webs that provide an area more easily deformed, as well as, connection and structural support between nodes.

Some devices exist to form or shape plates, but some are difficult to use and/or don't give the surgeon optimal forming or shaping control. Ideally, to form the plate, it is optimal to rotate or torque a node in one or more of the X, Y or Z axis while at least one other node is held firmly in place and isolated from the bending forces. This is particularly important if the node that the surgeon wants to isolate has already been affixed to the bone with a screw; otherwise, the bending forces will transmit to the screw and potentially cause pull-out of the same or damage to the bone. In some existing devices and methods, such as disclosed by Huebner in U.S. Pat. No. 7,189,237 the bending forces are not applied at the node, but instead are applied at the internodes or webs. This approach does not fully isolate a node where a screw has been placed from the bending forces, since the node itself is not held firmly. In other existing devices, the node that the surgeon may want to isolate would be held in place by threading a tool or a tool accepting socket into that node. However, this becomes a practical impossibility if a screw has already been affixed to the bone in that node, because the screw occupies the space and the thread where the tool or the tool accepting socket would normally be threaded. That precludes the possibility of isolating a node that has already been affixed to the bone from bending forces.

BRIEF SUMMARY OF THE INVENTION

It is accordingly an object of the invention to provide a formable bone plate, a node clamping apparatus, an osteotomy system and a method for reconstructing a bone, which overcome the above-mentioned disadvantages of the heretofore-known devices of this general type and which allow a user to easily shape osteotomy plates before, during or after affixing the plate to the bones, thus enabling an improved surgical procedure and a result that is superior to that possible with current devices. The clamping apparatus is intended to be used on the nodes of a plate according to the invention to facilitate optimum clamping.

The in-situ formable bone plates, node clamping apparatus and osteotomy system according to the invention are constructed in such a way that an appropriately constructed clamp can engage at least one node of the plate while the plate is affixed, partially affixed or not affixed, to the bone. In a preferred embodiment, the plate has a circumferential undercut around each node, where the undercut may or not extend along the internode portions. Correspondingly, in this embodiment, the clamp is constructed in such a way that it will first open, then be placed around a plate's node, and then closed to clamp circumferentially around the node, with a portion of the clamp extending under the undercut portion. This geometry permits secure fixation in all three X-Y-Z axes, permitting forming of the plate in any of these directions. The clamp may, optionally, have a "through hole" drilled through the center to serve as a drill guide during surgical procedures. In this configuration, the clamp is opened, placed around a node, and then clamped into place. Once clamped, the surgeon inserts a drill into the through hole of the clamp and proceeds to drill through the bone. The hole created by such drilling then serves as a pilot hole for a screw to be placed later. Additionally, the clamp of the instant embodiment is constructed to clamp around a node which may already have a screw affixing it to the bone. If desired, the clamp may have a recessed area in the corresponding region where the head of such a screw would normally be positioned when affixed to provide space relief and avoid interference of the screw head. An additional benefit of the presently described embodiment is that the smaller surface area of the plate, created by the undercut, may minimize tissue damage of the periosteum. It is believed that minimizing contact of plate to bone reduces the localized ischemia that may develop subsequent to plate application. Alternate embodiments include plate and clamp features that ensure clamping and three-axis articulation by other measures including usage of engagement holes and pins, and alternate configurations for circumferential clamping around the nodes.

The plates of the invention have the advantage of being easily formed by the surgeon to match the patient's anatomical circumstances before application, during application or after being partially or fully affixed in-situ.

Clamps made in accordance with an embodiment of the instant invention are constructed to mate with the plate geometry and selectively and securely hold nodes of a plate. In one particular method of the present invention, a first clamp is attached to a first node and, while holding it securely in position, a second clamp is attached to a second node and rotated in any, or all, of the X-Y-Z axes to form the plate into a desired configuration. Even in a case where the first node has been attached to the bone with a screw, the first clamp isolates the bending forces exerted by the rotation of the second clamp, preventing those forces from being translated to the screw and possibly causing pullout of the same and/or damage the bone. Therefore, using the system and method of the instant invention, it is possible to readjust the plate after screw application and to bend and contour the plate on each internode section during application.

In one particular embodiment of the instant invention, the plates are provided with "head" portions usually applied at the metaphysis or joint-end of the bone and "shaft" portions usually applied to the shaft of those bones. If desired, a "neck" portion can join the head and the shaft, for strength, but also for ease of shaping. Osteotomies and fusions are usually performed at the junction of the metaphysis with the shaft. The bendable internode sections and neck of the instant embodiment will allow the adjustment of the angle of correction after the plate has been completely applied.

The plates according to the invention have the capacity to be easily shaped ex-situ, that is, before application to the bone; and in-situ, that is, contoured to the bone during placement, and also allow a final correction to be made to their shape after they have been finally affixed to the bone. The plates also present the ability to accept compression, fixed angle and/or variable angle screws.

The plates according to a preferred embodiment of the invention are constructed to fit common reconstructive clinical needs and present dedicated deformable sections for correction adjustment. If desired, they may additionally have fixed angle K-wire holes for facilitating implant application or allow the use of K-Tacks for the same purpose.

The plates according to the invention come in basic shapes that allow the surgeon to easily cut them to length leaving a biologically acceptable cut surface.

If further desired, the plates according to the invention can also be provided with a step-compression/distraction mechanism to facilitate lengthening and shortening of bones.

Note that the plates according to the invention can be made in different sizes and shapes such as, but without being limited to, the examples enumerated below:
1. Plates for radial and ulnar osteotomy using, for example, 3.5/2.5 mm screws for stepped compression-distraction with dedicated head portions and for carpal bone fixation for arthrodesis/ligament repair using arched and circular shapes and 2.5 mm screws.
2. Plates for metacarpal osteotomy using 2.5 mm screws, which are straight with a head portion.
3. Plates for phalangeal osteotomy using 2.0 mm screws, which are straight with a head portion.
4. Plates for a scaphoid reconstruction device.
5. Plates for a total wrist fusion device.

Other features which are considered as characteristic for the invention are set forth in the appended claims.

Although the invention is illustrated and described herein as embodied in a formable bone plate, a clamping apparatus, an osteotomy system and a method for reconstructing a bone, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiments when read in connection with the accompanying drawings.

BRIEF DESCRIPTION OF THE SEVERAL VIEWS OF THE DRAWING

FIG. 1 is a diagrammatic, top-plan view of a first embodiment of an in-situ formable bone plate according to the invention having undercuts on the bottom surface of the plate;

FIG. 2 is a perspective view of the bone plate shown in FIG. 1;

FIG. 3 is a side-elevational view of the bone plate shown in FIGS. 1 and 2;

FIG. 4 is an enlarged, cross-sectional view of the bone plate, taken along the line IV-IV of FIG. 3, in the direction of the arrows;

FIG. 5 is an enlarged, top-plan view of the bone plate shown in FIGS. 1-4;

FIGS. 6A, 7A, 8A, 9A, 10A, 11A and 12A are top-plan views of different nodes of the bone plate shown in FIG. 5 and FIGS. 6B, 7B, 8B, 9B, 10B, 11B and 12B are respective cross-sectional views taken along the lines VI-VI to XII-XII of FIGS. 6A, 7A, 8A, 9A, 10A, 11A and 12A, showing different embodiments of undercuts of the bone plate;

FIG. 13A is a top-plan view of a second embodiment of an in-situ formable bone plate according to one particular embodiment of the invention having similar undercuts on the top surface and the bottom surface of the plate.

FIG. 13B is a perspective view of the plate shown in FIG. 13A.

FIG. 13C is a cross-sectional view taken along the lines XIII of FIG. 13A.

FIGS. 14A and 14B are top-perspective and bottom-perspective views of the bone plate shown in FIGS. 1-5;

FIG. 15 is a perspective view of a clamp fitted to a T-shaped bone plate with screws;

FIG. 16 is an enlarged, fragmentary, perspective view of a portion XVI of FIG. 15;

FIGS. 17 and 18 are respective front-perspective and side-perspective views of the clamp fitted to the T-shaped bone plate having compression screws;

FIG. 19 is a longitudinal-sectional view taken along the line XIX-XIX of FIG. 17, in the direction of the arrows;

FIG. 20 is an enlarged, fragmentary, longitudinal-sectional view of a portion XX of FIG. 19;

FIGS. 24 and 25 are respective side-elevational and front-elevational views of the clamp showing a drill guide thereof;

FIG. 26 is an enlarged, fragmentary, side-elevational view of a portion XXVI of FIG. 24;

FIG. 27 is a longitudinal-sectional view taken along the line XXVII-XXVII of FIG. 26, in the direction of the arrows;

FIG. 28 is a perspective view of a T-shaped bone plate, compression screw and K-wire on a bone segment;

FIG. 29 is an enlarged, fragmentary, perspective view of a portion XXIX of FIG. 28;

FIG. 30 is a side-elevational view of the K-wire;

FIG. 31 is a perspective view of the K-wire;

FIG. 32 is an enlarged, fragmentary, perspective view of a portion XXXII of FIG. 31;

FIGS. 33, 34 and 35 are respective top-plan, side-elevational and perspective views of another embodiment of an in-situ formable bone plate according to the invention, having engagement holes;

FIG. 36 is an enlarged, fragmentary, perspective view of a portion XXXVI of FIG. 35;

FIG. 37 is an enlarged, fragmentary, side-elevational view of a portion XXXVII of FIG. 34;

FIG. 37 is an enlarged, fragmentary, side-elevational view of a portion XXXVII of FIG. 34;

FIG. 38 is a cross-sectional view taken along the line XXXVIII-XXXVIII of FIG. 37, in the direction of the arrows;

DETAILED DESCRIPTION OF THE INVENTION

Figure 22:
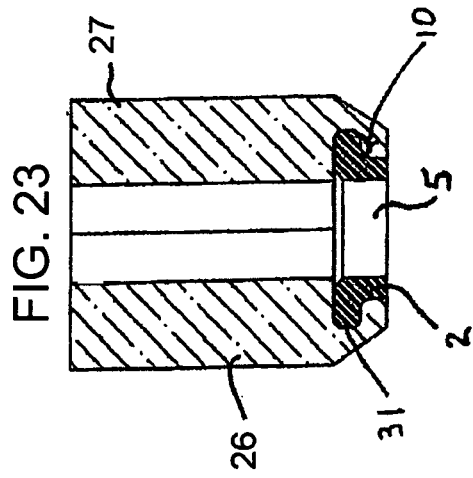
FIG. 22 is an enlarged, fragmentary, end-elevational view of a portion XXII of FIG. 21.

Referring now to the figures of the drawings in detail and first, particularly, to FIGS. 1-4 thereof, there is seen a first embodiment of a bone plate 1 according to one particular embodiment of the invention, having a plate body with seven nodes 2 and webs or internodes 3, therebetween. However, this is not meant to be limiting, as the bone plate 1 may have more or fewer than seven nodes, as desired, and may be linear, T-shaped, L-shaped, Y-shaped, arched, curved or any combination of shapes, as will be discussed further below. The nodes 2 each have an inner surface 4, which can be spherical, aspherical, frustoconical, cylindrical or any other geometric shape as required for seating or engaging the complementarily shaped head of a screw, surrounding a hole 5 for permitting passage of the shaft of a screw 23, as is best seen in FIGS. 15 and 16. Each node 2 also has a clamp engagement section 6, as will be discussed further below.

FIG. 5 shows a bone plate 1' with nodes 2 and internodes or webs 3, while FIGS. 6A to 12B each show a possible form of a node 2 of the bone plate 1' in respective top-plan and cross-sectional views. More specifically, FIGS. 6A and 6B show a node 2 without an engagement section, for purposes of comparison. FIGS. 7A and 7B show a node 2 with an engagement section in the form of an annular or circumferential step 10. FIGS. 8A and 8B show a node 2 with an engagement section in the form of two radial blind holes 11. FIGS. 9A and 9B show a node 2 with an engagement section in the form of four oblique blind engagement holes 12. FIGS. 10A and 10B show a node 2 with an engagement section in the form of a concave annular or circumferential V-shaped radial recess 13. FIGS. 11A and 11B show a node 2 with an engagement section in the form of two L-shaped undercuts 14. FIGS. 12A and 12B show a node 2 with an engagement section in the form of frustum surface 15 of a cone. It is noted in this regard that the engagement section with the engagement holes 12 shown in FIGS. 9A and 9B are intended to cooperate with a clamp 40 designed in accordance with one particular embodiment of the invention discussed below. It must also be understood that more than one, or even all, of the nodes may have engagement sections. The node configurations 2 of the plate 1' shown in FIGS. 6A-12A are examples of possible node configurations consistent with the present invention. However, it can be seen from the foregoing that additional node configurations and geometries are possible for the nodes 2, while still remaining within the scope of the instant invention.

FIGS. 13A and 13B show a second embodiment of bone plate 1 with nodes 2 and internodes or webs 3, inner surface 4, which can be spherical, aspherical, frusto-conical, cylindrical or any other geometric shape as required for seating or engaging the complementarily shaped head of a screw, surrounding a circular hole 5 or elongated slot 5' for permitting passage of the shaft of a screw. FIG. 13C shows a cross section of a node 2 with an engagement section conformed by a convex annular or circumferential V-shaped radial projection 16. The engagement section is symmetrical which allows the plate to be used with its upper or lower surface, indistinctly, adjacent to the bone.

FIGS. 14A and 14B are respective top and bottom perspective views of a bone plate 1 according to one particular embodiment of the invention, having the nodes 2, the internodes 3, the inner surfaces 4 and the screw holes 5. The plate 1 can have a variety of shapes and/or geometries in accordance with the instant invention. For example, a T-shaped bone plate 21 having a leg 21', a crosspiece 21" and nodes 2, is shown in FIG. 15. Referring now to FIG. 15, it may be seen that a clamp 20 in accordance with one embodiment of the instant invention is placed over, and engages with, a node 2, thus receiving a head 22 of a screw 23 passing through a hole 5 in one of the nodes 2. From FIG. 16 it can be seen that the head of each screw 23 has a socket 24. The sockets 24 have polygonal, for example hexagonal, hexalobular or multilobular, surfaces for receiving a driver, wrench or screwdriver for tightening and loosening the screws. FIGS. 15 and 16 also show that the present particular embodiment of the clamp 20 has clamping jaws 26, 27 engaging the bone plate 21 and a clamping tube 28 sliding over and holding the clamping jaws 26, 27 in place. The clamping jaws 26, 27 each have a respective relief 26', 27' and the clamping tube 28 has a drill guide hole 29 and a handle 30. The drill guide hole 29 continues through the clamping jaws 26, 27 to permit drill access to the bone as seen in FIGS. 19 and 20.

FIGS. 17 and 18 respectively show the clamp 20 from the side of the T-shaped bone plate 21 and from the end of the T-shaped bone plate 21, screwed into a bone 32 by the screws 23. Screws 23 may be compression screws, fixed angle and/or variable angle screws, as desired. FIG. 19 is a cross section that shows the clamping tube 28 and the handle 30 and FIGS. 19 and 20 show the drill guide hole 29 and illustrate how the jaws 26, 27 engage the node 2 receiving the head 22 of screw 23.

Figure 23:
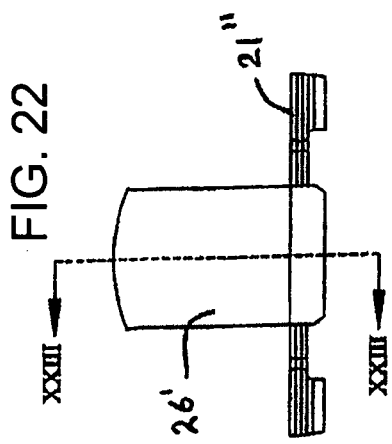
FIG. 23 is a longitudinal-sectional view taken along the line XXIII-XXIII of FIG. 22, in the direction of the arrows.
Figure 21:
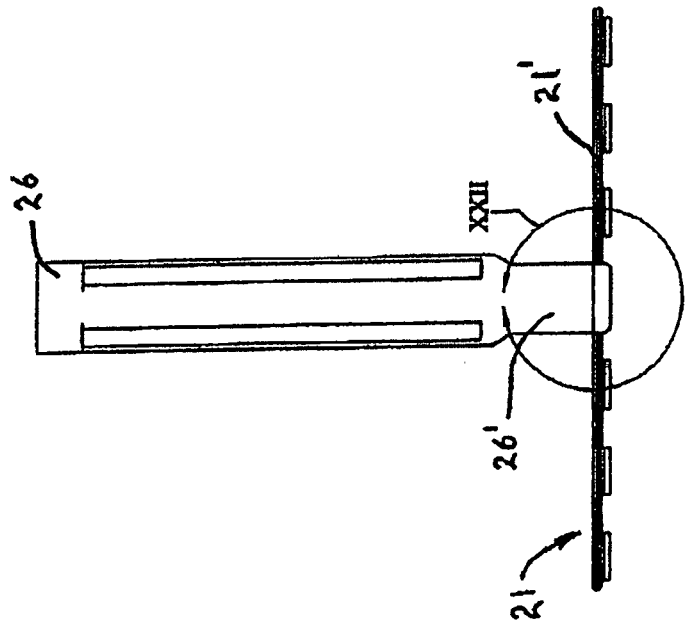
FIG. 21 is a side-elevational view of the bone plate and the clamp with a clamping tube removed.
Figure 41:
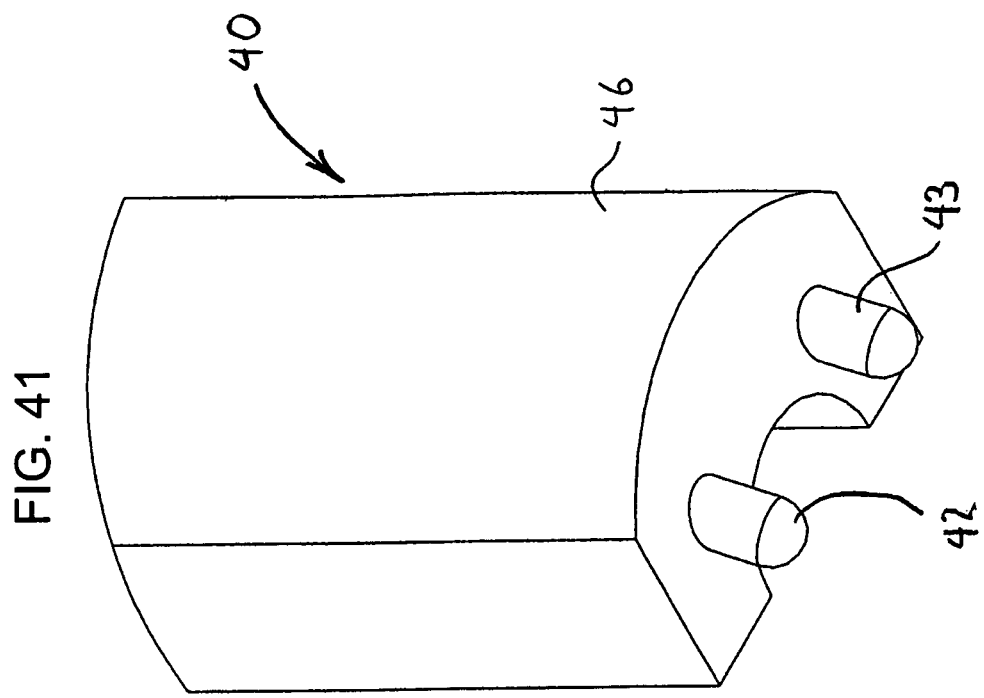
FIG. 41 is an enlarged, fragmentary, perspective view of the clamp of FIGS. 39 and 40.
Figure 40:
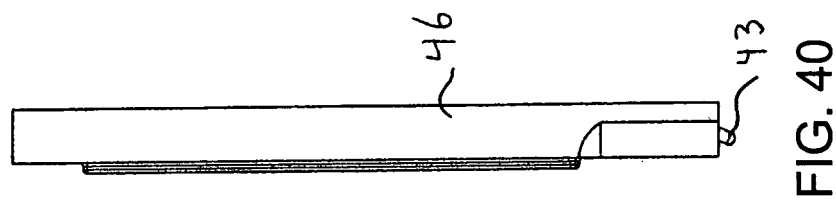
FIGS. 39 and 40 are respective side-elevational and front-elevational views of a further embodiment of a clamp in accordance with the present invention having engagement pins.
Figure 39:
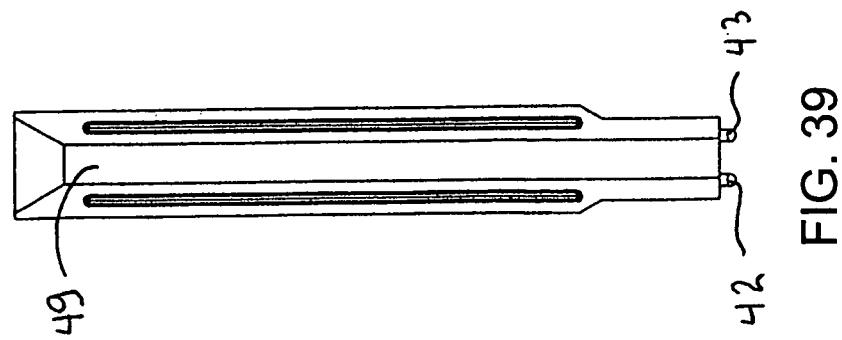
Figure 42:
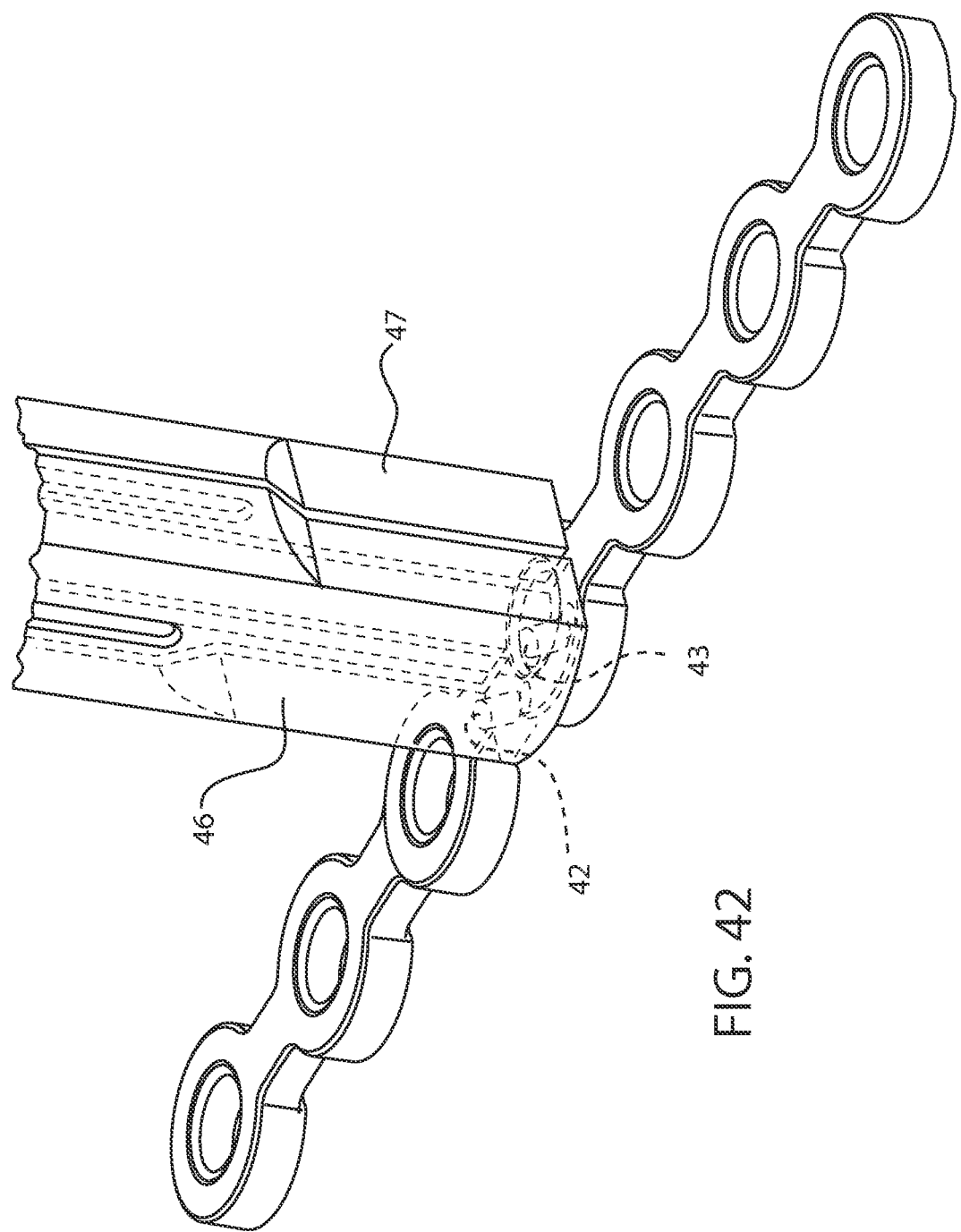
FIG. 42 is an enlarged, fragmentary, perspective view of the clamp of FIGS. 39-41 engaging the bone plate of FIGS. 33-38.

FIGS. 21 and 22 show a side view elevation of one of the clamping jaws 26 with relief 26' disposed over a node 2 of the bone plate 21. FIG. 23, in a manner similar to FIG. 20, shows how the clamping jaws 26, 27 engage a node 2 nested therein by gripping the annular or circumferential step 10 of the engagement section shown in FIGS. 7A and 7B. In FIGS. 24 and 25 the clamp locking features 35, 36 on both sides of the drill guide hole 29 are intended to assist in aligning the two parts as they come together and prevent the clamping jaws from sliding apart once clamped. The locking features may also be accomplished with holes and pins. A socket 31, shaped to engage a node 2 is nested in the step 10, is additionally seen in FIGS. 26 and 27. The socket may include a screw head relief 31' to avoid interference of a screw head and permit proper engagement of socket 31 into node 2 if a screw has been placed in that node.

Figure 45:
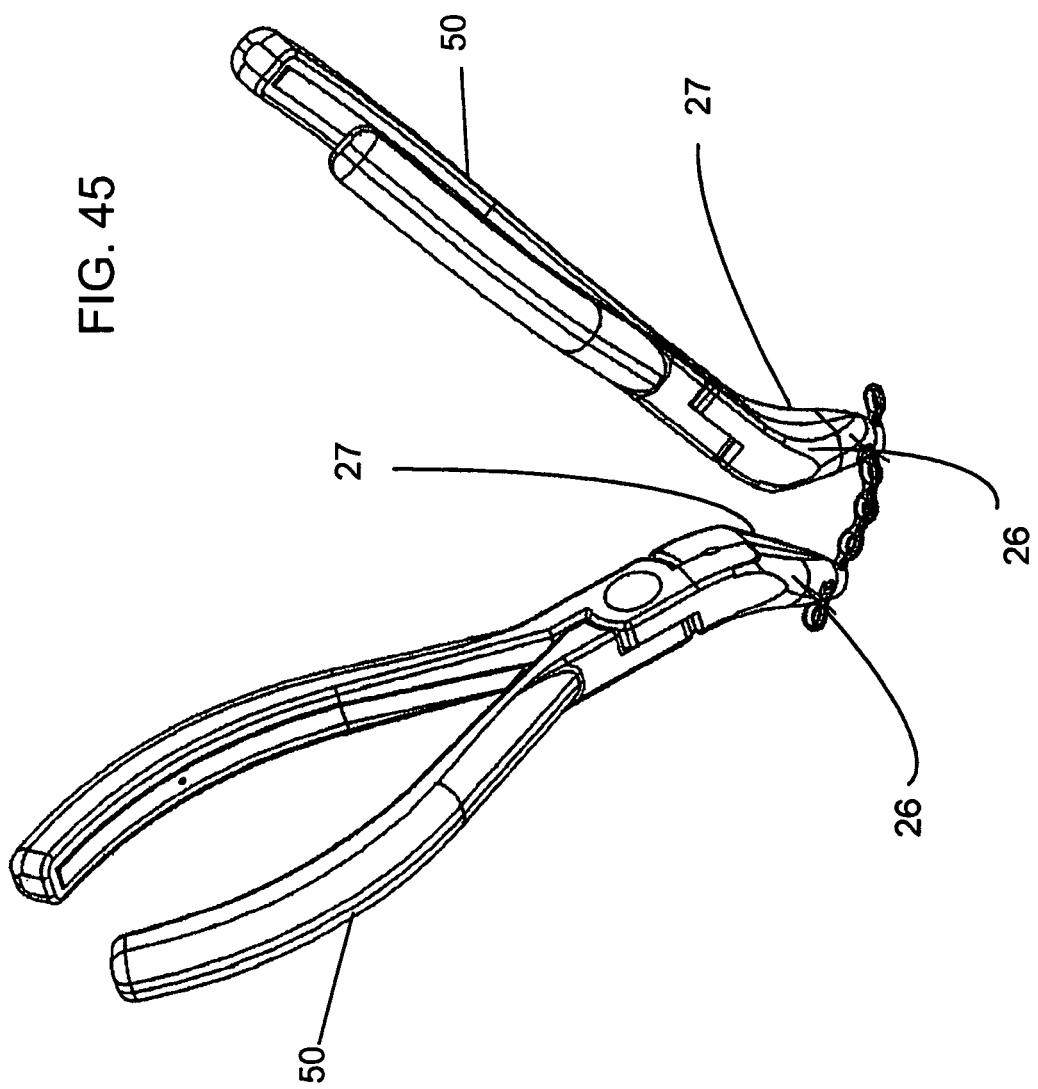
FIG. 45 is a perspective view of a further embodiment of the instant invention including clamps where the jaws are built into the distal end of a pliers.

Referring to FIGS. 19, 20, 23, 24, 25, 26 and 27, a clamp 20 is used by placing jaws 26, 27 having lower ends with sockets 31 that are complementary to one of the engagement sections 10, 11, 13, 14, 15, 16 shown in FIGS. 7B-12B and FIG. 13C around a node 2, so as to engage the engagement section. The clamping tube 28 of FIG. 18 is then slid over the jaws to lock them in place by aligning locking features 35, 36. Alternatively, as seen in FIG. 45 the clamping jaws 26, 27 may be implemented as the distal jaws of pliers 50 which are locked in place by the action of compressing the proximal handles of the pliers 50.

FIG. 28 shows a K-wire or Kirschner wire 38 inserted through a node 2 of the bone plate 21 into a bone 32 as a temporary anchor, as well as a screw 23, for example, a compression screw, attaching the bone plate to the bone. The K-wire 38 is shown in side and oblique-elevational views in FIGS. 30 and 31 and the enlarged illustration of FIG. 32 shows that a button 39 is attached to the K-wire 38 and a self-drilling tip 37 is formed at the end of the K-wire. As is seen in FIG. 29, the button 39 fits the contour of surface 4 while allowing a portion of the K-wire 38 to pass through the hole 5. The button 39 is intended to prevent the K-wire 38 from penetrating the bone more than necessary for achieving temporary anchoring.

A further embodiment of the bone plate and clamp of the present invention is illustrated in FIGS. 33-44. In contrast to the previously described embodiments of the invention, which use a clamp 20 having sockets 31 matching engagement sections 10, 11, 13, 14, 15 and 16 at the lower surface or lateral surface of a plate 1, 21, the presently described embodiment uses a clamp 40 having engagement pins 42, 43 that engage the four oblique blind engagement holes 12 of the plate. See also, for example, engagement holes 12 of the engagement section shown in FIGS. 9A and 9B.

More specifically, FIGS. 33, 34, 35 and 36 show a bone plate 41 having a plate body with nodes 2 including the oblique blind engagement holes 12 and internodes or webs 3 between the nodes 2. The nodes 2 each have an inner surface 4 surrounding a hole 5 for accepting a screw. The actual oblique direction of the engagement holes 12 is best seen in the cross-sectional views of FIGS. 37 and 38.

Figures 43, 44:
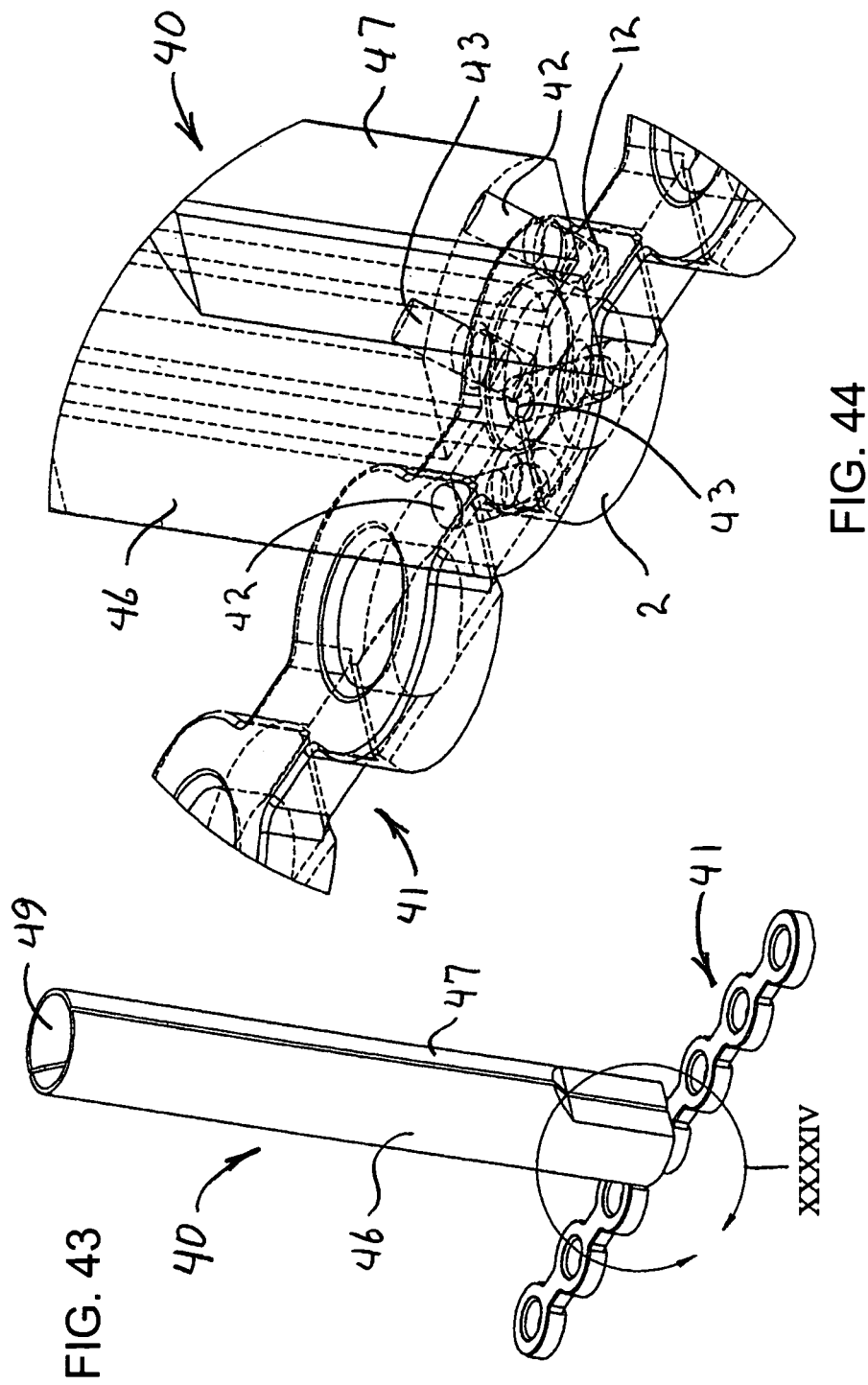
FIG. 43 is a perspective view of the clamp and bone plate of FIG. 42.
FIG. 44 is a fragmentary, perspective view of a portion XXXXIV of FIG. 43, showing the engagement pins and holes.

Referring now to FIGS. 43 and 44, the clamp 40 once again has two clamping jaws 46, 47 surrounding a drill guide hole 49 and the engagement pins 42, 43 protruding from the clamping jaws, as is better seen in FIGS. 39, 40, 41 and 42. FIGS. 43 and 44 illustrate how the engagement pins 42, 43 of each clamping jaw 46, 47 of the clamp 40 engage the oblique engagement holes 12 in a node 2 of the bone plate 41. The clamping tube 28 of FIGS. 17, 18 and 19, which for simplicity is not illustrated in FIGS. 33-44, is slid over the clamping jaws 46, 47 to lock them in place, after placing the engagement pins 42, 43 in the engagement holes 12 of a node 2. As additionally described in connection with the other embodiments, the clamping jaws 46, 47 of the present embodiment may be implemented by the distal jaws of pliers 50 which are locked into place by compressive action on the proximal pliers handles, as shown more particularly in FIG. 45.

Referring now to FIGS. 1-45, a system of the invention operates as follows: A clamp 20, 40, 50 can engage the plate 1, 1', 21, 41 while the plate is affixed, partially affixed or not affixed at all to the bone. A first clamp 20, 40, 50 is opened, then placed circumferentially around a node, with a portion of the clamp extending under the undercut portion or surface or into the lateral recesses or holes or with the engagement pins into the engagement holes. This secures the first node 2 assuring that any bending forces created by rotating or torqueing will be transmitted to the first clamp 20, 40, 50, shielding any screw 23 which may be present at the first node 2 from these forces, thereby prohibiting screw 'pull-out'. Then, a second clamp 20, 40, 50 is opened and secured in a similar way to a second node 2. Rotating or torqueing the second clamp generates bending forces which cause bending or formation of the plate in the direction of any of the X, Y, and/or Z axes.

In particular embodiments of the invention, a drill guide hole 29, 49 in the center of the clamp 20, 40 serves as a drill guide during surgical procedures. After a clamp 20, 40 has been clamped into place, the surgeon inserts a drill into the guide hole 29, 49 of the clamp 20, 40 and proceeds to drill through the bone. The hole created by such drilling then serves as a pilot hole for a screw 23 to be placed later. Additionally, the clamp 20, 40, 50 is constructed to clamp around a node 2 which may already have a screw 23 affixing it to the bone. The plates 1, 1', 21, 41 of the invention have the advantage of being able to be formed by the surgeon to match the patient's anatomical circumstances before application, during application or after being partially or fully affixed in-situ. The clamps 20, 40, 50 of the invention are constructed to mate with the plate geometry and selectively and securely hold the nodes 2 of a plate. Bending the plate 1, 1', 21, 41 with a clamp 20, 40, 50 while another clamp 20, 40, 50 is attached and held in position firmly at a node 2 isolates the bending forces preventing them from being translated to the screws 23. It is possible to readjust sections of the plate 1, 1', 21, 41 after screw application and to bend and contour the plate at each internode section 3 during application. The bending internode sections of the plates of the instant invention allow the adjustment of the angle of correction even after the plate has been completely applied. The plates, made in accordance with the instant invention can be easily shaped in-situ, that is, contoured to the bone during placement, and a final correction can be made after they have been finally attached to the bone with screws. Thus, the plates of the invention present the ability to accept compression, fixed angle and/or variable angle screws. The plates fit common reconstructive clinical needs and present dedicated deformable sections for correction adjustment. Additionally, as described herein, holes may be included for K-wires, to facilitate implant application and allow the use of K-Tacks with limiting buttons, for the same purpose.

The invention claimed is:

1. An osteotomy system, comprising:
   a formable bone plate including:
      a plate body having a plurality of nodes and internodes between said nodes,
      said nodes having holes formed therein for receiving screws or wires to be screwed or placed into a bone, and
      at least two of said nodes having an engagement section; and
   means for bending said formable bone plate, including:
      a first means for engaging the engagement section of a first of said at least two of said nodes having an engagement section;
      a second means for engaging the engagement section of a second node of said at least two of said nodes having an engagement section, said engagement section of said second node configured to transmit at least a portion of a force applied to said second means for engaging, to said second node, when said second means for engaging is engaged with said engagement section of said second node; and
   said formable bone plate configured such that at least one internode between said first node and said second node bends in one or more of the X, Y and Z axes when a force is applied by said second means for engaging to said second node while said first means for engaging is engaged with and holds said first node immovable.

2. The osteotomy system according to claim 1, wherein each of said first and second means for engaging include:
   two distal clamping jaws, each having a socket;
   a clamping tube to be slid over said two distal clamping jaws for locking said two distal clamping jaws in place at said engagement sections, and
   a handle attached to said clamping tube.

3. The osteotomy system according to claim 2, wherein said clamping jaws and said clamping tube have a drill guide hole formed therein for guiding a drill bit for drilling into the bone for later placement of a screw.

4. The osteotomy system according to claim 2, wherein said engagement section is an annular or circumferential portion formed in a lower surface of said at least two nodes, and said sockets are configured for engaging said portion.

5. The osteotomy system according to claim 4, wherein said annular or circumferential portion is a V-shaped radial recess formed in a lateral surface of said at least two nodes, and said sockets have a complementary V-shaped circumferential projection for circumferentially engaging said recess.

6. The osteotomy system according to claim 4, wherein said annular or circumferential portion is a V-shaped radial projection formed in a lateral surface of said at least two nodes, and said sockets have a complementary V-shaped circumferential recess for circumferentially engaging said projection.

7. The osteotomy system according to claim 4, wherein said annular or circumferential portion is an L-shaped undercut formed in a lower surface of said at least two nodes, and said sockets have a complementary L-shaped circumferential projection for circumferentially engaging said undercut.

8. The osteotomy system according to claim 4, wherein said annular or circumferential portion is a frustoconical recess formed in a lateral surface of said at least two nodes, and said sockets have a complementary frustoconical circumferential projection for circumferentially engaging said recess.

9. The osteotomy system according to claim 1, wherein at least one of said nodes has an inner surface surrounding said hole for seating the head of a screw.

10. The osteotomy system according to claim 1, wherein:
    said first and second means for engaging each include pliers handles extending proximally from each one of two distal clamping jaws; and
    said pliers handles being arranged to, upon squeezing of said pliers handles, cause said two distal clamping jaws of said means for engaging to lock around said engagement sections; and
    said pliers handles additionally being arranged to transmit a force applied to said pliers handles of said means for engaging to a portion of said engagement sections locked by said two distal clamping jaws.

11. The osteotomy system according to claim 10, wherein said clamping jaws have a drill guide hole formed therein for guiding a drill bit for drilling into the bone for later placement of a screw.

12. A method for bone reconstruction, which comprises the following steps:
    a) providing a formable bone plate including a plate body having a plurality of nodes, internodes between the nodes, holes in the nodes for receiving screws or wires to be screwed or placed into a bone and an engagement section at least at two of said nodes;
    b) providing a a means for bending the formable bone plate including at least first and second means for engaging an engagement section of first and second ones of said at least two of said nodes having an engagement section;
    c) engaging a first of the two means for engaging around the engagement section of a first node and holding the first node immovable relative to an underlying bone; and
    d) engaging a second of the two means for engaging around the engagement section of a second node, and bending at least one internode between the first node and the second node in at least one of the X, Y and Z axes to conform the formable bone plate to the underlying bone, by applying a force to the second means for engaging, at least a portion of which force is transmitted to the second node, while holding the first node immovable relative to the underlying bone with the first means for engaging.

13. The method of claim 12, further including the steps of: before engaging the second means for engaging around the engagement section of the second node:
    e) drilling a hole into the underlying bone through a drill guide hole in clamping jaws of the first means for engaging;
    f) placing a screw into a hole in the first node and screwing the screw into the drilled hole, thereby affixing, at the first node, the formable bone plate to the underlying bone.

14. The method of claim 13, wherein steps c), d), e) and f) are repeated for a plurality of nodes, such that all nodes desired to be affixed to the underlying bone are affixed to the underlying bone.

* * * * *